United States Patent
Gill

(10) Patent No.: US 10,610,674 B2
(45) Date of Patent: *Apr. 7, 2020

(54) NEUROSURGICAL APPARATUS

(71) Applicant: RENISHAW (IRELAND) LIMITED, Swords (IE)

(72) Inventor: Steven S Gill, Bristol (GB)

(73) Assignee: RENISHAW (IRELAND) LIMITED, Wotton-under-Edge (GB)

( * ) Notice: Subject to any disclaimer, the term of this patent is extended or adjusted under 35 U.S.C. 154(b) by 20 days.

This patent is subject to a terminal disclaimer.

(21) Appl. No.: 15/657,792

(22) Filed: Jul. 24, 2017

(65) Prior Publication Data

US 2017/0319831 A1    Nov. 9, 2017

Related U.S. Application Data

(63) Continuation of application No. 14/348,942, filed as application No. PCT/EP2012/004150 on Oct. 4, 2012, now Pat. No. 9,802,028.

(30) Foreign Application Priority Data

Oct. 4, 2011 (GB) .................................. 1117061.0

(51) Int. Cl.
  *A61M 39/02* (2006.01)
  *A61M 27/00* (2006.01)
  *A61M 25/02* (2006.01)

(52) U.S. Cl.
  CPC ...... *A61M 27/006* (2013.01); *A61M 39/0247* (2013.01); *A61M 2025/0213* (2013.01);
  (Continued)

(58) Field of Classification Search
  CPC ........ A61M 27/006; A61M 2025/0213; A61M 2039/025; A61M 39/0247
  See application file for complete search history.

(56) References Cited

U.S. PATENT DOCUMENTS

| 3,333,588 A | 8/1967 | Schulte |
| 4,646,752 A | 3/1987 | Swann et al. |

(Continued)

FOREIGN PATENT DOCUMENTS

| EP | 0402571 A1 | 12/1990 |
| GB | 2357700 A | 7/2001 |

(Continued)

OTHER PUBLICATIONS

Apr. 7, 2015 Office Action issued in Chinese Patent Application No. 201280048724.2.

(Continued)

*Primary Examiner* — Kai H Weng
(74) *Attorney, Agent, or Firm* — Oliff PLC

(57) ABSTRACT

A high-strength steel sheet and a method for manufacturing a high-strength steel sheet having excellent phosphatability and excellent corrosion resistance after electrodeposition coating has been performed, even in the case where the contents of Si and Mn are high. The method may comprise annealing a steal sheet by using a continuous annealing method, performing a heating process, controlling the maximum end-point temperature of a steel sheet in the annealing furnace, controlling the traveling time of the steel sheet, and controlling the dew point of the atmosphere.

18 Claims, 3 Drawing Sheets

(52) U.S. Cl.
CPC ............... *A61M 2039/025* (2013.01); *A61M 2039/0282* (2013.01)

(56) References Cited

U.S. PATENT DOCUMENTS

| | | | |
|---|---|---|---|
| 4,995,856 | A | 2/1991 | Heindl et al. |
| 5,098,411 | A | 3/1992 | Watson et al. |
| 5,800,390 | A | 9/1998 | Hayakawa et al. |
| 6,609,020 | B2 | 8/2003 | Gill |
| 8,128,600 | B2 | 3/2012 | Gill |
| 2002/0065508 | A1 | 5/2002 | Borgesen |
| 2003/0220604 | A1 | 11/2003 | Al-Anazi |
| 2004/0102761 | A1 | 5/2004 | Ahmed |
| 2005/0043673 | A1 | 2/2005 | Lieberman |
| 2007/0260222 | A1 | 11/2007 | Kraus |
| 2008/0262319 | A1 | 10/2008 | Reichenberger et al. |
| 2009/0198218 | A1 | 8/2009 | Gill et al. |
| 2009/0264811 | A1 | 10/2009 | Asfora |
| 2010/0228179 | A1* | 9/2010 | Thomas ............... A61M 27/006 604/9 |
| 2010/0318061 | A1 | 12/2010 | Derrick et al. |
| 2010/0318064 | A1 | 12/2010 | Derrick et al. |
| 2011/0282319 | A1 | 11/2011 | Gill |

FOREIGN PATENT DOCUMENTS

| | | |
|---|---|---|
| JP | 2007-301363 A | 11/2007 |
| JP | 2009-279433 A | 12/2009 |
| TW | I260232 B | 8/2006 |
| WO | 03/007784 A2 | 1/2003 |
| WO | 2006/039501 A2 | 4/2006 |

OTHER PUBLICATIONS

May 4, 2016 Office Action issued in U.S. Appl. No. 14/348,942.
Aug. 30, 2016 Office Action issued in Japanese Patent Application No. 2014-533789.
Feb. 8, 2017 Office Action issued in U.S. Appl. No. 13/348,942.
Jan. 27, 2017 Office Action issued in European Patent Application No. 12 778 230.8.
Jan. 9, 2012 Search Report issued in British Patent Application No. GB1117061.0.
Dec. 3, 2012 International Search Report issued in International Patent Application No. PCT/EP2012/004150.
Dec. 3, 2012 Written Opinion issued in International Patent Application No. PCT/EP2012/004150.
Jul. 28, 2017 Notice of Allowance issued in U.S. Appl. No. 14/348,942.
Apr. 19, 2018 Office Action issued in European Patent Application No. 12 778 230.8.

* cited by examiner

NEUROSURGICAL APPARATUS

This application is a Continuation of Application No. 14/348,942, filed Apr. 1, 2014, which in turn is a National Phase of PCT/EP2012/004150, filed Oct. 4, 2012, which claims priority to GB 1117061.0, filed Oct. 4, 2011. The entire contents of the prior applications are hereby incorporated by reference herein in their entirety.

The present invention relates to cerebral shunt apparatus. In particular, the present invention relates to a cerebral catheter device and associated apparatus suitable for draining fluid from the brain ventricles (e.g. to treat hydrocephalus) or from cysts.

The implantation of a shunt to drain cerebrospinal fluid (CSF) from a lateral ventricle of the brain is a well established neurosurgical procedure. This procedure is typically performed to treat hydrocephalus. Typical ventricular shunt apparatus comprises an elongate, flexible, catheter formed of silicone material. To insert such ventricular shunt apparatus a hole is drilled in the skull and a pathway is then forged through brain tissue to a lateral ventricle. The formation of the passageway is typically performed by hand using a long rigid probe element. The elongate silicone catheter is then inserted down the preformed pathway to the lateral ventricle of the brain from which fluid is to be drained. Once inserted, the implanted catheter tubing is connected, typically via a one-way valve, to a subcutaneously buried drainage tube that terminates in the peritoneal cavity or the right atrium of the heart. In this manner, CSF and other fluids can be vented from the ventricles of the brain thereby allowing the pressure of CSF in the brain to be reduced.

Many tens of thousands of ventricular shunt systems are implanted each year, but a large proportion of these shunts become blocked within a relatively short period of time. It has been estimated that approximately 40% of ventricular shunt related surgical procedures are to rectify problems arising from previous procedures. This problem is particularly prevalent in children where proximal catheter obstruction in small ventricles is common and growth of the brain and skull causes the position of the shunt within the brain to vary over time.

In the functional neurosurgery area, guide tubes for guiding electrodes, fine drug dispensing catheters and other neurosurgical instruments to precisely defined target sites within the brain parenchyma have been proposed previously. For example, see the present inventor's previous U.S. Pat. No. 6,609,020.

According to a first aspect of the present invention, there is provided a cerebral catheter device for draining fluid from the brain of a patient, comprising;

an elongate tube for insertion into the brain of a patient to a vicinity of a desired target, and a head attached to the elongate tube, wherein the head has a passageway therethrough in fluid communication with a lumen of the elongate tube and formations are provided on the external surface of the head for securing the head in a hole formed in the skull of a patient, wherein the head further comprises a first fluid connector portion that is attachable to an associated drainage catheter device thereby allowing fluid communication to be established between the lumen of the elongate tube and a drainage catheter device via the passageway of the head.

The present invention thus provides a cerebral catheter device that can be used as part of a cerebral shunt system for draining fluid from the brain of a patient. In particular, the cerebral catheter device may be used to drain CSF from a lateral ventricle of the brain to treat hydrocephalus (e.g. following a head injury). The cerebral catheter device may also be used to drain fluid from tumour cavities, abscesses and cysts. As mentioned below, the cerebral catheter device may also be used to monitor pressure or to deliver fluids to the brain.

The cerebral catheter device includes an elongate tube for insertion into the brain of a patient to a vicinity of a desired target. For example, the tip of the elongate tube may be guided into a lateral ventricle of the brain using a stereotactic or neurosurgical robot based procedure. The length of the elongate tube is preferably preselected (e.g. cut to length) based on knowledge of the position of the target site in the brain and the position of the burr hole relative to that target. During insertion, the formations provided on the outside of the head of the cerebral catheter device can engage (e.g. press fit into) the burr hole as the tip of the elongate tube reaches the target site. The head can thus secure the cerebral catheter device firmly in place and ensure that the tip does not wander from the target site during subsequent parts of the procedure in which drainage catheter devices etc. are connected. The head may also form a seal with the bone of the skull and thereby provide a barrier against bacteria entering the brain though the burr hole; this seal can also improve with time as bone osseointegrates with the head.

The head further comprises a first fluid connector portion that is attachable to an associated drainage catheter device. In other words, the first fluid connector portion of the head allows an associated drainage catheter device to be connected to the cerebral catheter device. This arrangement permits fluid communication to be established between the lumen of the elongate tube and a drainage catheter device via the passageway of the head. Fluid can thus be drained from the elongate tube, through the head and into an associated drainage catheter device.

The cerebral catheter device of the present invention has a number of advantages over known cerebral catheters that are used for ventricular shunt applications. As mentioned above, the head of the device is firmly attached into a burr hole of the skull and osseointegrates with the skull over time; this provides a barrier to infection that may otherwise grow along the outside of the drainage tubing and enter the brain. The size of burr hole required when implanting a cerebral catheter device of the present invention can also be significantly smaller than that needed for implanting prior art devices. The cerebral catheter device can also be quickly inserted into the brain using a surgical guidance device thereby removing or at least significantly reducing the need to handle the device. Such a non-contact procedure also reduces the risk of bacteria being introduced into the brain on the implanted cerebral catheter device. In addition, the precise placement of the tip of the elongate tube means that the chances of shunt blockage can be reduced by avoiding regions of the brain such as the choroid plexus. The present invention thus provides an improved cerebral catheter device and hence a cerebral shunt system that is less likely to require replacement or repair.

The elongate tube may comprise a plurality of apertures. For example, one or more apertures may be provided in the side wall of the elongate tube. Advantageously, an end opening is provided at the distal tip of the catheter.

Preferably, only such an end opening is provided (i.e. there may be no apertures in the side walls of the elongate tube). This enables the elongate tube to be easily cut to length (e.g. dependent on the target site distance from the burr hole). The elongate tube may have more than one lumen; in which case the elongate tube may then comprise at least one aperture for each lumen. Advantageously, the elongate tube has only a single lumen. Providing only a single lumen avoids entrapment of the choroid plexus in side holes and high flow rates through a large aperture is less likely to result in blockages.

The formations provided on the external surface of the head may be of any type that enable the head to be attached to a burr hole formed in the skull. For example, the formations may define a screw thread. The screw thread may allow the head to be screwed into a burr hole. The formations preferably comprise ridges or protrusions that allow the head to be affixed to a hole formed in the skull by a press-fit action. The use of a press-fit attachment simplifies the procedure and immediately ensures tight engagement of the head in the bur hole. The formations may define a screw thread and the head may be press fitted into the burr hole. The screw thread can then be used when removing the device; e.g. the device can be removed by unscrewing it from the skull. One or more features (e.g. a slot or pin holes) may be provided for engaging a removal tool (e.g. a screw driver or a pin holding tool). The formations may alternatively provide a means for the head to be attached to the skull using bone screws or the like. An adhesive or bone cement may be used in combination with the formations to secure the head to the skull.

The elongate tube may have an outer diameter greater than 1 min. More preferably, the elongate tube has an outer diameter greater than 2 mm, or more preferably greater than 3 mm. If a 3 mm outside diameter is provided, the internal diameter is preferably greater than 2.5 mm.

In order to avoid blockages (e.g. from blood clots or other debris) or the deposition of protein, it is preferable for the internal diameter of the passageway through the head to be substantially the same as the internal diameter of the elongate tube. Any attached drainage catheter device may also have a lumen of a similar internal diameter. The internal surface of the elongate tube and or passageway may also be coated with a material (e.g. a diamond like carbon, DLC, coating) that reduces the adhesion of material to the internal surface defining the fluid pathway.

The elongate tube may be formed from, or coated with, any suitable biocompatible material. Advantageously, the elongate tube is sufficiently stiff so as to remain substantially straight after implantation. Conveniently, the elongate tube comprises a material having a surface that has low adhesion to brain tissue. In other words, the elongate tube may be made from a material that has a relatively slippery surface and doesn't substantially adhere to brain tissue. Suitable materials include PTFE or a polyurethane plastic such as Carbothane (Registered Trade Mark) as manufactured by the Lubrizol Corporation, Ohio, USA. Polyurethane plastic is particularly advantageous because it minimises the build-up of biofilm that can lead to encrustation. The use of such a material is advantageous compared with traditional shunt materials, such as silicone, which are relatively tacky and adhere to brain tissue. The elongate tube and/or head of the cerebral catheter device is preferably CT visible; for example, a plastic may be impregnated with Barium to make it visible to x-ray based imaging techniques.

The first fluid connector portion may be formed in a variety of ways that provide a reliable, leak free, fluid connection with an associated second fluid connector portion of a drainage catheter device. Preferably, the first fluid connector portion comprises a conical recess formed in the head that surrounds an aperture in fluid communication with the passageway. In this manner, a conical protrusion of the second fluid connector portion can be pushed into the conical recess formed in the head to provide the required fluidic connection. The first and/or second fluid connector portion may, if necessary, comprise a resiliently deformable washer or the like for providing a tight fluidic seal.

The first and second fluid connector portions may also provide a mechanical connection between the cerebral catheter device and the catheter drainage device. In other words, the drainage catheter device may be secured to the skull via the connection between the second fluid connector portion and the first fluid connector portion. Alternatively, a separate mechanical attachment mechanism may be provided. For example, the second fluid connector portion may include means for mechanical attachment to the skull. For example, the second fluid connector portion may include one or more protruding flanges having holes through which bone screws may be passed. The second fluid connector portion may then be screwed directly to the skull thereby ensuring tight engagement of the first and second fluid connector portions is maintained.

It should be noted that although the cerebra/catheter device of the present invention is primarily intended to be used as a drainage catheter, it could also be used for other purposes. For example, the cerebral catheter device could also be used as a tube to guide instruments (fine catheters, electrodes, biopsy needles etc) into the brain. An endoscope could also be passed through the cerebral catheter device to check where distal end is located. Drugs or fluids could also be pumped through the cerebral catheter device into the brain. The cerebral catheter device could also be connected to a pressure monitoring device to measure CSF pressure within the brain. It should also be noted that more than one cerebral catheter device may be implanted in a patient.

The present invention also extends to cerebral shunt apparatus that that comprises a cerebral catheter device as described above. The apparatus preferably also includes a drainage catheter device. The drainage catheter device conveniently comprises a second fluid connector portion for engaging the first fluid connector portion of the cerebral shunt device to provide fluid communication between the drainage catheter device and the elongate tube via the passageway through the head. In other words, the drainage catheter device may connected to the cerebral catheter device to allow fluid to be drained therefrom.

The second fluid connector portion is preferably releasably attachable to the first fluid connector portion. This allows a second fluid connector portion to be attached to, and detached from, the first fluid connector portion of the cerebral catheter device as required. This is advantageous as it means the drainage catheter device can be repaired or replaced without having to disturb the cerebral catheter device. As mentioned above, the first and second fluid connector portions may also mechanically attach the drainage tube to the head. It is, however, preferable for the second fluid connector portion to include separate means for attachment to the skull (such as flanges for receiving bone screws). En particular, the drainage catheter device preferably comprises one or more features for attachment to the skull, wherein attachment to the skull maintains the second fluid connector in tight engagement with the first fluid connector. Advantageously, the one or more features for attachment to the skull comprise flanges having apertures for receiving bones screws, the bone screws thereby holding the second connector portion in tight engagement with first connector portion.

The cerebral shunt apparatus preferably comprises a valve. The valve may comprise a one-way valve to stop the flow of fluid back into the brain. The valve may be a pressure control valve and/or a flow control valve. Advantageously, the valve includes an anti-siphon mechanism. The valve may be incorporated in the head of the cerebral shunt device. Preferably, the valve forms part of the drainage catheter device. The valve may then be located at any convenient point along the drainage tube of the drainage catheter device, but it is preferably located near the cerebral shunt device. The valve may thus be replaced or repaired without removal of the cerebral shunt device. The valve may be a valve of the type produced by Medronic Inc., Minneapolis, Minn., US.

The drainage catheter device may also comprise drainage tubing. For example, drainage tubing may run from the second connector portion to the valve and from the valve to the peritoneal cavity or the right atrium of the heart. In this manner, fluid collected from the brain with the cerebral shunt device may be vented into the peritoneal cavity or circulatory system. For acute procedures, the fluid may be drained into an external bag.

It is preferred that the elongate tube of the cerebral catheter device is advanced along a straight pathway to the desired target in the brain. The cerebral shunt apparatus may thus comprise a guide wire for stiffening the elongate tube during insertion of the cerebral catheter device into the brain of the patient. Preferably, the elongate tube of the cerebral catheter device is linear and the central axis of the tube is coincident with the central axis of the passageway through the head. This allows the guide wire to be inserted through the cerebral catheter device without having to be bent. The cerebral catheter device may also be inserted into the brain by sliding it over a pre-inserted guide wire.

The cerebral shunt apparatus may also comprise a neurosurgical guidance device. For example, the apparatus may comprise a stereotactic delivery system or a neurosurgical robot, such as the Neuromate (Registered Trade Mark) robot sold by Renishaw Mayfield SA. The cerebral shunt apparatus may also include a reservoir; e.g. a dome shaped reservoir that is attachable to the first fluid connector portion of the cerebral catheter device.

According to a further aspect of the invention, a method is provided of inserting a cerebral catheter device comprising an elongate tube and a head into the brain of a subject, the method comprising the steps of; inserting the elongate tube to a vicinity of a desired target through a burr hole formed in the skull, securing the head in the burr hole, and collecting or delivering fluid via the lumen of the elongate tube. Pressure sensors may also be provided.

Preferably, the method comprises the step of inserting the elongate tube into a lateral ventricle of the brain. The frontal horn of a lateral ventricle may targeted. Advantageously, the method comprises removing fluid (e.g. CSF and/or blood) from the ventricle. The method may also involve use of any of the apparatus described above.

A ventricular shunt device is also described herein that comprises a length of tube, wherein one or more apertures are provided at the distal end of the tube and the tube comprises polyurethane plastic. The polyurethane plastic may be Carbothane. The length of tube may be formed from polyurethane plastic. The length of tube may comprise an external and/or internal coating of polyurethane plastic. Polyurethane plastic is particularly advantageous because it minimises the build-up of biofilm that can lead to encrustation.

The invention will now be described, by way of example only, with reference to the accompanying drawings in which.

Figure 1:
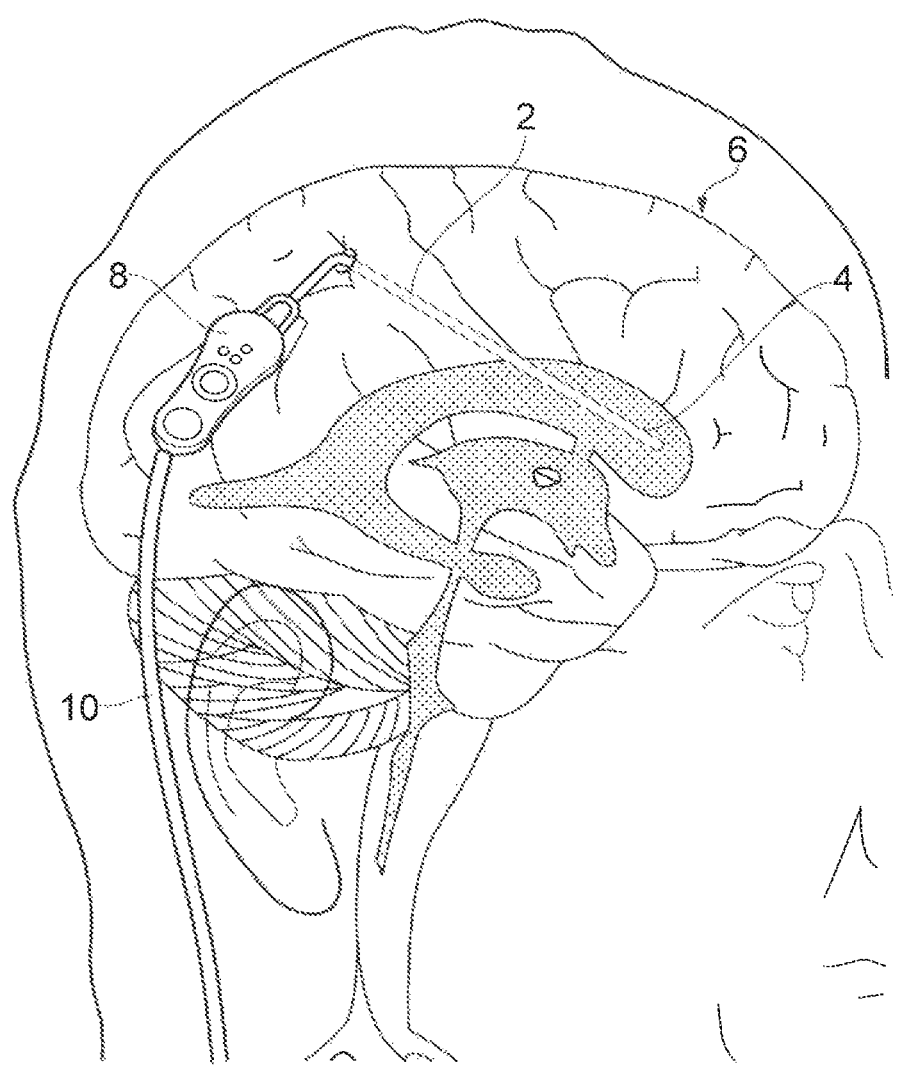
FIG. 1 shows a prior art silicone ventricular shunt system.

Referring to FIG. 1, prior art ventricular shunt apparatus is illustrated. The shunt apparatus includes a cerebral catheter device 2 in the form of a length of elastic silicone tubing. The distal end of the cerebral catheter device 2 is placed within a lateral ventricle 4 of the brain 6 and comprises a plurality of apertures in its side wall (not shown) for collecting CSF.

A typical procedure for implanting the catheter device 2 comprises making an incision in the scalp and forming a burr hole (typically 10-15 mm in diameter) through the skull. An elongate rod or probe is then manually inserted into the brain by the surgeon and guided, by hand, into the lateral ventricle using external anatomical landmarks for guidance. The probe is then withdrawn and the distal end of the cerebral catheter device 2 is pushed down the passageway that has been formed in the brain tissue until its distal end reaches the lateral ventricle.

The proximal end of the catheter device 2 protrudes through the burr hole formed in the skull and is connected to a one-way valve 8 by a bayonet connector. The proximal end of the catheter device is also sutured to the bayonet connector to ensure a robust physical connection. A further length of tubing 10 runs from the a one-way valve 8 to the peritoneal cavity or to the right atrium of the heart.

Once implanted, the shunt apparatus is all buried subcutaneously. However, shunt apparatus of this type has been found to fail for a number of reasons and it is estimated that around 40% of all shunt procedures relate to replacing or repairing previously implanted apparatus. The inventor has become aware of a number of reasons for such failure. For example, the small apertures formed in the side wall of the distal end of the cerebral catheter device 2 can become blocked relatively easily. This is especially the case when the distal end of the cerebral catheter device 2 is located in or near the choroid plexus. In addition, the manual insertion process can lead to placement of the catheter device 2 in a sub-optimal location. Furthermore, the extensive manual handling of the catheter device that is typically required during the procedure can result in bacteria being carried by the device and introduced into the brain; this can lead to infection. It is also possible for infection to "grow" along the length of the tubing 10; for example bacteria may collect on the tube from the skin during implantation and pass into the brain.

Figure 2:
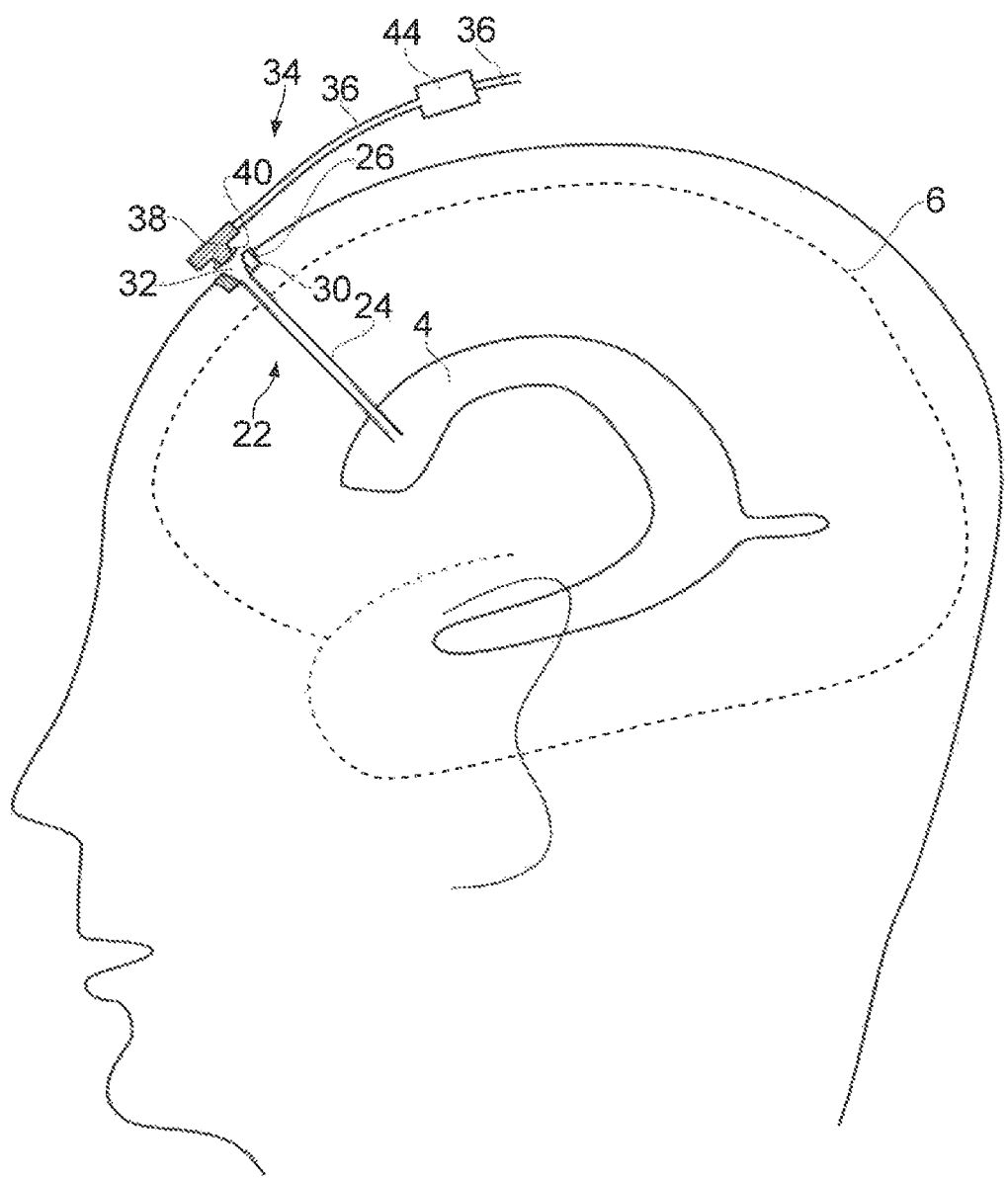
FIG. 2 shows ventricular shunt apparatus in accordance with the present invention.
Figure 3:
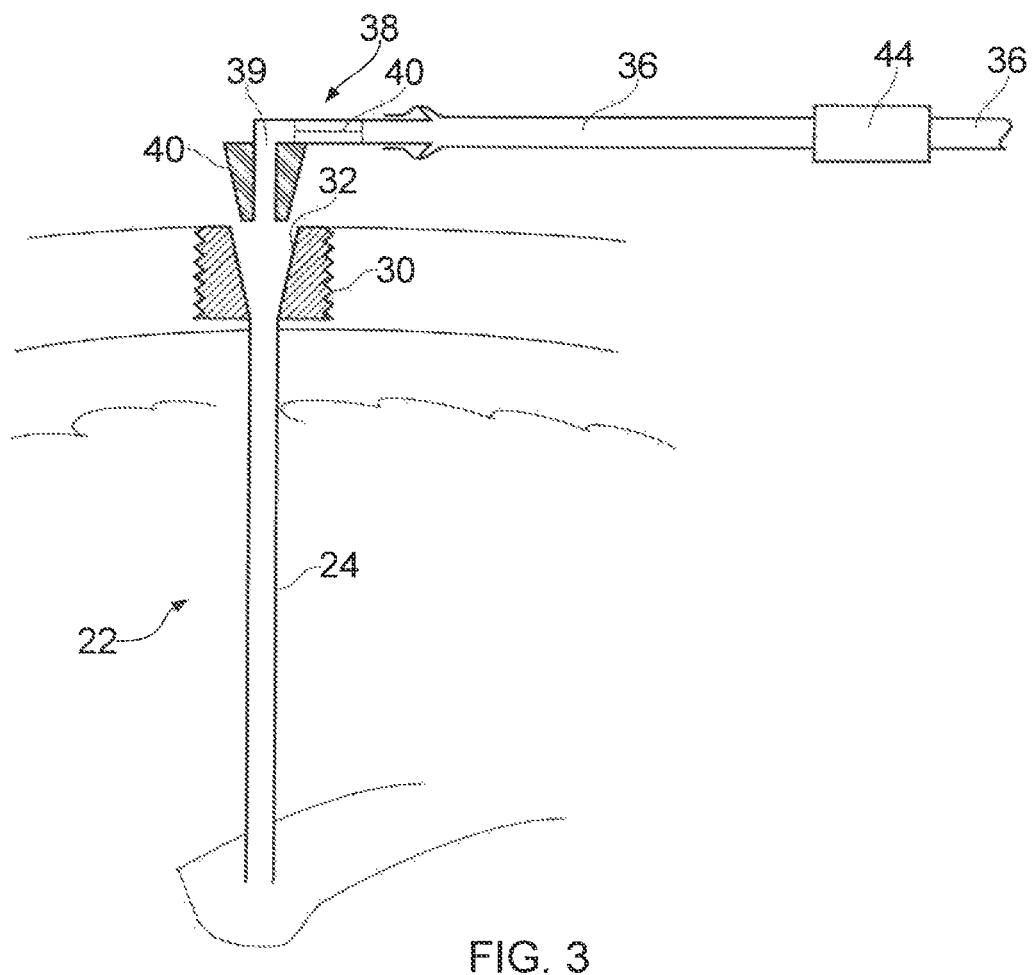
FIG. 3 shows in more detail the fluid connector of ventricular shunt apparatus of FIG. 2.
Figure 4:
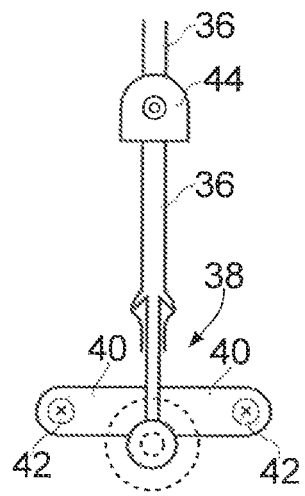
FIG. 4 is a perspective view of the apparatus shown in FIGS. 2 and 3.

FIGS. 2 to 4 illustrate cerebral shunt apparatus 20 of the present invention. The cerebral shunt apparatus 20 comprises a cerebral catheter device 22 and a drainage catheter device 34.

The cerebral catheter device 22 comprises a length of polyurethane plastic tubing 24. A head 26 is provided at the proximal end of the tubing 24 and an opening 28 is provided at the distal end of the tubing 24. Although only a single opening is shown at the tip, it would also or alternatively be possible to provide one or more apertures in the side wall at the distal end of the tubing 24. The head 26 comprises one or more formations, such as a ridges or protrusions, on its outer surface that allow it to be secured in place in a burr hole formed in the skull of the patient by a press fit action. Although press-fitting of the head 26 into a hole formed in the skull is illustrated, it should be noted that other attachment means could be used. For example, the head 26 could include formations that form a screw thread for screwing the head 26 into skull. The head 26 could also be glued in place. The head 26 also comprises a passageway 30 therethrough which is in fluid communication with the lumen of the plastic tubing 24. The passageway 30 also comprises a first fluid connector portion 32 in the form of a fluted, conical, opening for connection to the drainage catheter device 34. Preferably, the tubing 24 and head 26 are formed integrally, for example by a moulding process.

The drainage catheter device 34 comprises drainage tubing 36 having a second fluid connector portion 38 at its proximal end. The second fluid connector portion 38 comprises a conical protruding portion 40 that is dimensioned to engage with the opening of the first fluid connector portion 32. A passageway 39 through the second fluid connector portion 38 establishes fluid communication between the drainage tubing 36 and an opening of the conical protruding portion 40. The distal end of the draining tubing 36 can be placed, as is known in the art, in the peritoneal cavity or the right atrium of the heart.

In use, the conical protruding portion 40 of the second fluid connector portion 38 is pushed into the opening of the first fluid connector portion 32 to provide a fluid connection. A seal (not shown), such as an o-ring seal, may be provided if necessary to ensure a tight fluidic seal between the first and second connector portions. The second fluid connector portion 38 comprises wings 40 (see FIG. 4) that extend in a direction substantially parallel to the skull. The wings 40 include holes 42 through which bone screws are passed to secure the second fluid connector portion 38 to the skull. This maintains tight engagement of the conical protruding portion 40 in the opening of the first fluid connector portion 32, although other attachment means are possible.

The drainage catheter device 34 also comprises a one-way, anti-siphon, valve 44 to control the flow of fluid extracted via the cerebral catheter device 22. The valve 44 is provided part way along the drainage tube 36 but is preferably close to the cerebral catheter device 22. The valve 44 may also include one or more features that can be manipulated through the scalp; for example, a pump feature for clearing debris from the tubing may be provided. Any valve of known type may be used, such as a valve from the Medtronic range.

The cerebral catheter device 22 may be inserted into the patient using a variety of surgical procedures. These may include free hand insertion techniques, but it is preferred that guided neurosurgical techniques are used. A guide wire may be used to stiffen the cerebral catheter device 22 during insertion. For example, the stereotactic technique described in WO03/07784 for implanting a guide tube could be used to implant the cerebral catheter device 22. It would also be possible to use other, known, stereotactic insertion methods. Image guided and robot surgery could also be used to place the tip of the cerebral catheter device 22 at the vicinity of the required target in a lateral ventricle of the brain. Any such technique may conveniently be used to place the tip of the cerebral catheter device 22 in the frontal horn of a lateral ventricle, in a position that avoids the choroid plexus.

The invention claimed is:

1. A cerebral shunt apparatus, comprising:
    a cerebral catheter device configured for draining fluid from the brain of a patient, comprising:
        an elongate tube configured for insertion into the brain of the patient to a vicinity of a desired target, and
        a head attached to the elongate tube, the head having a passageway therethrough in fluid communication with a lumen of the elongate tube and formations comprising ridges or a screw thread that are provided on the external surface of the head and that are configured for securing the head in a hole formed in the skull of the patient,
        the head further comprising a first fluid connector portion that is attachable to an associated drainage catheter device thereby allowing fluid communication to be established between the lumen of the elongate tube and the drainage catheter device via the passageway of the head; and
    the drainage catheter device comprising a length of flexible drainage tubing and having a second fluid connector portion configured to engage the first fluid connector portion of the cerebral catheter device to provide fluid communication between the drainage catheter device and the elongate tube via the passageway through the head.

2. The apparatus according to claim 1, wherein the elongate tube has a single lumen with an aperture at the distal end thereof.

3. The apparatus according to claim 1, wherein the formations provided on the external surface of the head enable the head to be affixed to the hole formed in the skull by a press-fit action.

4. The apparatus according to claim 1, wherein the outer diameter of the elongate tube is greater than 1 mm.

5. The apparatus according to claim 1, wherein the internal diameter of the elongate tube is substantially the same as the internal diameter of the passageway through the head.

6. The apparatus according to claim 1, wherein the elongate tube is sufficiently stiff so as to remain substantially straight after implantation.

7. The apparatus according to claim 1, wherein the elongate tube comprises a material having a surface that has low adhesion to brain tissue.

8. The apparatus according to claim 7, wherein the elongate tube is formed from polyurethane plastic or PTFE.

9. The apparatus according to claim 1, wherein the first fluid connector portion comprises a conical recess formed in the head that surrounds an aperture in fluid communication with the passageway.

10. The apparatus according to claim 1, wherein the second fluid connector portion is releasably attachable to the first fluid connector portion.

11. The apparatus according to claim 1, wherein the drainage catheter device comprises one or more features configured for attachment to the skull, wherein attachment to the skull maintains the second fluid connector portion in tight engagement with the first fluid connector portion.

12. The apparatus according to claim 1, comprising a oneway valve.

13. The apparatus according to claim 12, comprising a guide wire for stiffening the elongate tube during insertion of the cerebral catheter device into the brain of the patient.

14. The apparatus according to claim 8, comprising a neurosurgical guidance device for guiding the distal end of the elongate tube to the desired target.

15. The apparatus according to claim 1, wherein the formations comprise the screw thread.

16. The apparatus according to claim 1, wherein from its uppermost end to its lowermost end, the outer surface of the head is substantially cylindrical.

17. A method of inserting a cerebral catheter device comprising an elongate tube and a head into the brain of a subject, the method comprising the steps of:

inserting the elongate tube to a vicinity of a desired target through a burr hole formed in the skull of the subject, securing the head in the burr hole, wherein the head comprises ridges or a screw thread that are provided on the external surface, attaching a drainage catheter to the head to place the drainage catheter in fluid communication with the lumen of the elongate tube, and collecting fluid via the drainage catheter and the lumen of the elongate tube.

18. The method according to claim 17, wherein inserting the elongate tube to the vicinity of the desired target includes inserting the elongate tube into the brain of the subject.

* * * * *